United States Patent
Wong

(10) Patent No.: US 7,197,784 B2
(45) Date of Patent: Apr. 3, 2007

(54) ELECTRIC TOOTHBRUSH

(75) Inventor: James Pong Chun Wong, Hong Kong (HK)

(73) Assignee: Truly Electronics Manufacturing Limited, Kwai Chung, New Territories (HK)

( * ) Notice: Subject to any disclaimer, the term of this patent is extended or adjusted under 35 U.S.C. 154(b) by 155 days.

(21) Appl. No.: 10/924,662

(22) Filed: Aug. 24, 2004

(65) Prior Publication Data

US 2005/0055784 A1    Mar. 17, 2005

(30) Foreign Application Priority Data

Sep. 16, 2003  (CH) .............................. 03 1 57148

(51) Int. Cl.
*A61C 17/227* (2006.01)

(52) U.S. Cl. .............................. 15/22.1; 15/28; 15/22.2

(58) Field of Classification Search ................. 15/22.1, 15/22.2, 28

See application file for complete search history.

(56) References Cited

U.S. PATENT DOCUMENTS

| 5,784,743 | A  | * | 7/1998 | Shek ........................... 15/22.1 |
| 6,721,986 | B2 | * | 4/2004 | Zhuan ......................... 15/22.2 |
| 6,920,660 | B2 | * | 7/2005 | Lam ........................... 15/22.1 |
| 2003/0154567 | A1 | * | 8/2003 | Drossler et al. ............. 15/22.1 |

* cited by examiner

*Primary Examiner*—Gladys J P Corcoran
*Assistant Examiner*—S Karls
(74) *Attorney, Agent, or Firm*—Alix, Yale & Ristas, LLP

(57) ABSTRACT

An electric toothbrush includes a casing having a handle and a neck extending from the handle. A motor is situated within the handle and has an output shaft with an eccentric cam on it. A tuft block is located at a remote end of the neck. A rocker arm extends longitudinally within the neck and has a proximal end driven by the cam, and a distal end driving the tuft block. A resilient bushing is sealed within the neck and intermediate-portion of the rocker arm extends through it in sealed manner to allow pivoting of the rocker arm across the bushing.

7 Claims, 4 Drawing Sheets

ELECTRIC TOOTHBRUSH

BACKGROUND OF THE INVENTION

The present invention relates to electric toothbrushes. More particularly, although not exclusively, the invention relates to an electric toothbrush having a longitudinal rocker arm that is mounted at an intermediate-position upon a flexible bushing within the toothbrush casing that serves not only to support the rocker arm to enable it to pivot thereupon, but also to seal electrical components within the toothbrush casing against ingress of liquid therepast.

Electric toothbrushes are known to comprise an angularly oscillating tuft block driven to oscillate by an electric motor and a transmission shaft. Sometimes, the transmission shaft rotates about its longitudinal axis. In other installations, a transmission rod reciprocates longitudinally.

A problem with the above electric toothbrushes is in sealing the shaft or rod to the toothbrush casing. Rotating shafts mounted within resilient seals wear the seals over a period as a result of sliding fictional contact between the rod and the seal, thereby causing unwanted leakage. Similarly, longitudinally oscillating rods cause wear within rubber seals as a result of fictional sliding contact therewith.

OBJECTS OF THE INVENTION

It is an object of the present invention to overcome or substantially ameliorate the above disadvantage and/or more generally to provide an improved electric toothbrush having a longitudinal rocker arm that is mounted at an intermediate-position upon a flexible bushing within the toothbrush casing that serves not only to support the rocker arm and enable it to pivot thereupon, but also to seal about the rocker arm in use preferably substantially without sliding contact therewith.

DISCLOSURE OF THE INVENTION

There is disclosed herein an electric toothbrush comprising:
- a casing comprising a handle and a neck extending from the handle,
- a motor situated within the handle and comprising an output shaft having an eccentric cam thereon,
- a tuft block at a remote end of the neck,
- a rocker arm extending longitudinally within the neck and having a proximal end driven by the cam, and a distal end driving the tuft block, and
- a resilient bushing sealed within the neck and through which an intermediate-portion of the rocker arm extends in sealed manner to allow pivoting of the rocker arm across the bushing.

Preferably, the toothbrush further comprises a cam follower mounted within the casing to reciprocate transversely therein, the cam follower cooperating with the cam and the rocker arm.

Preferably, the cam follower comprises a recess into which the cam extends.

Preferably, the cam follower comprises a transverse rod upon which the cam follower slides.

Preferably, the cam follower further comprises an aperture into which the proximal end of the rocker arm is received.

Preferably, the electric toothbrush further comprises a head attached to or formed integrally with the neck, and wherein the tuft block is mounted to pivot upon head and comprises a slot into which the distal end of the rocker arm is received.

Preferably, the distal end of the rocker arm is bulbous.

Preferably, the resilient bushing comprises an annular external groove and the neck comprises an annular internal ridge received by the groove.

BRIEF DESCRIPTION OF THE DRAWINGS

A preferred form of the present invention will now be described by way of example with reference to the accompanying drawings, wherein.

DESCRIPTION OF THE PREFERRED EMBODIMENT

Figure 1:
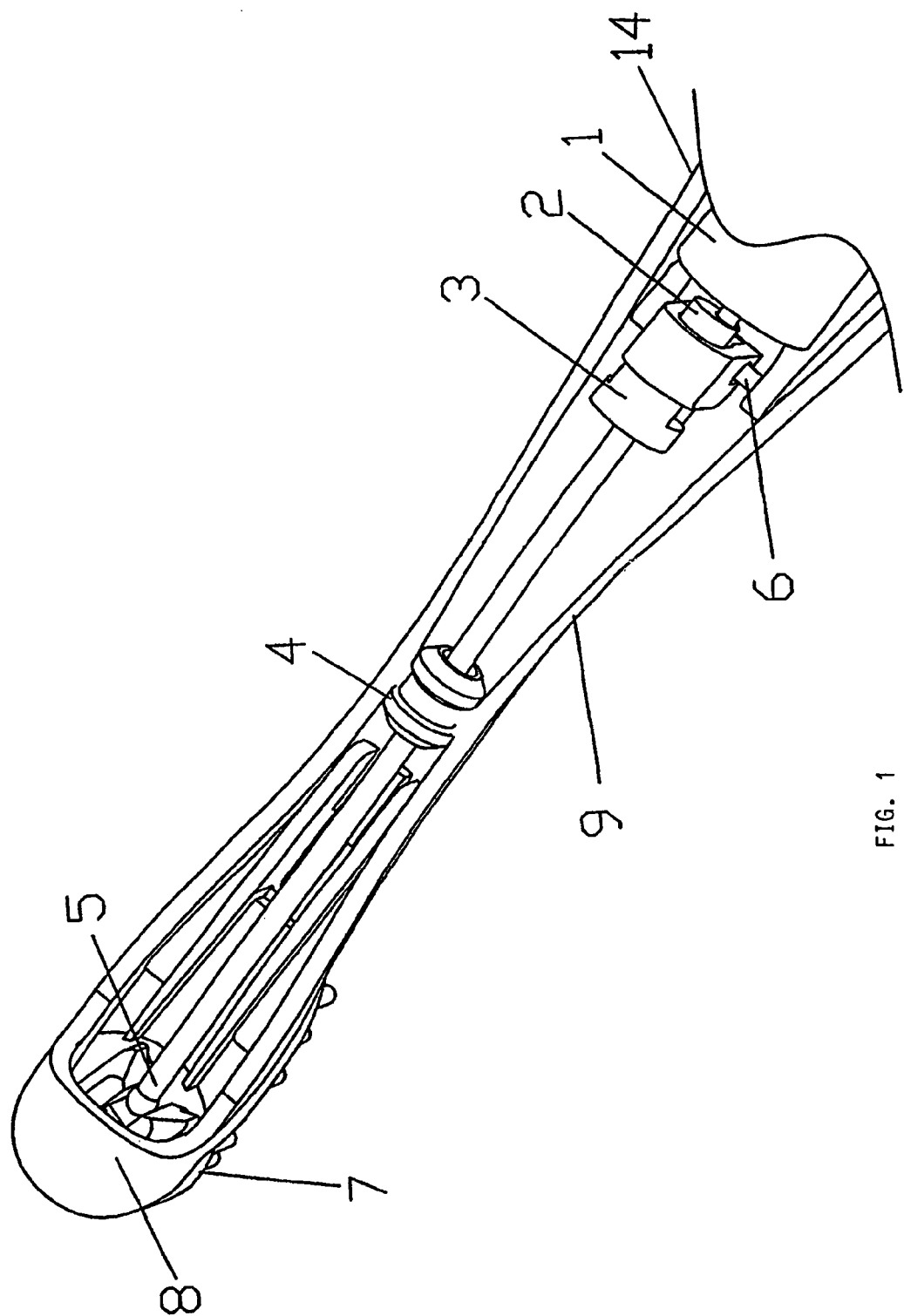
FIG. 1 is a schematic perspective cut-away illustration of a neck portion of an electric toothbrush.
Figure 2:
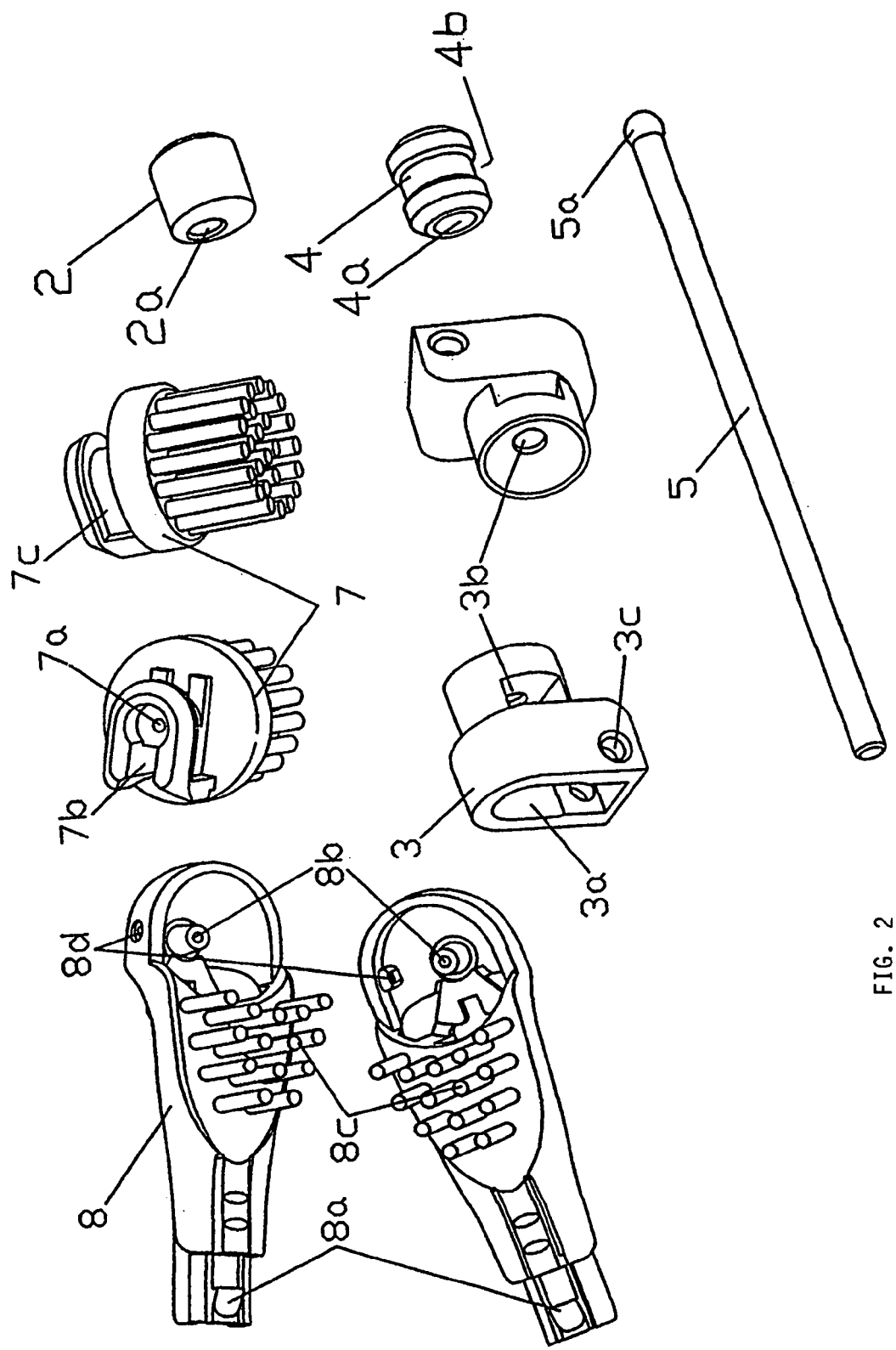
FIG. 2 is a schematic parts-exploded assembly illustration of component parts of the toothbrush head.
Figure 3:
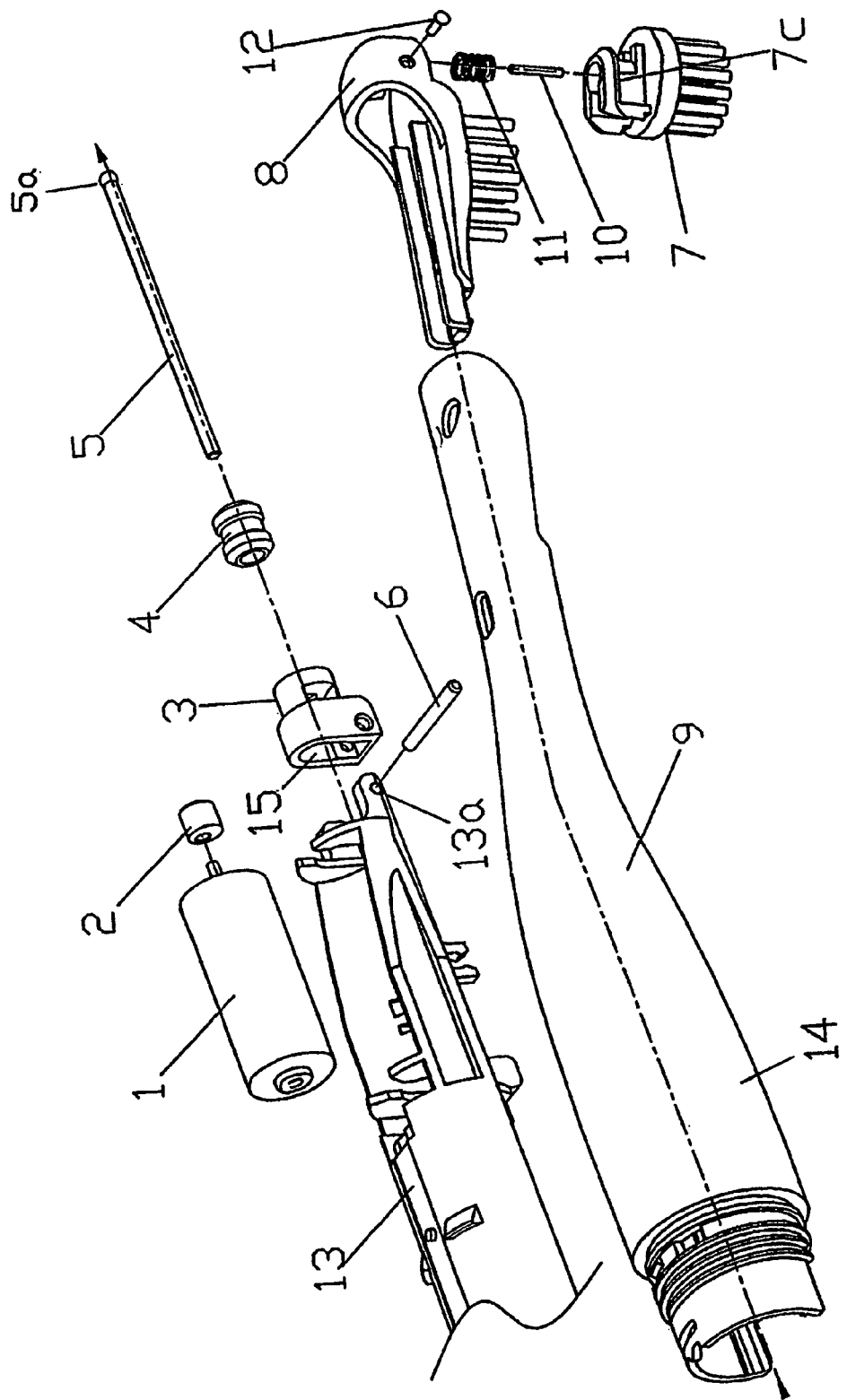
FIG. 3 is a schematic parts-exploded perspective illustration of component parts of the toothbrush the neck and handle.
Figures 4A, 4B, 4C:
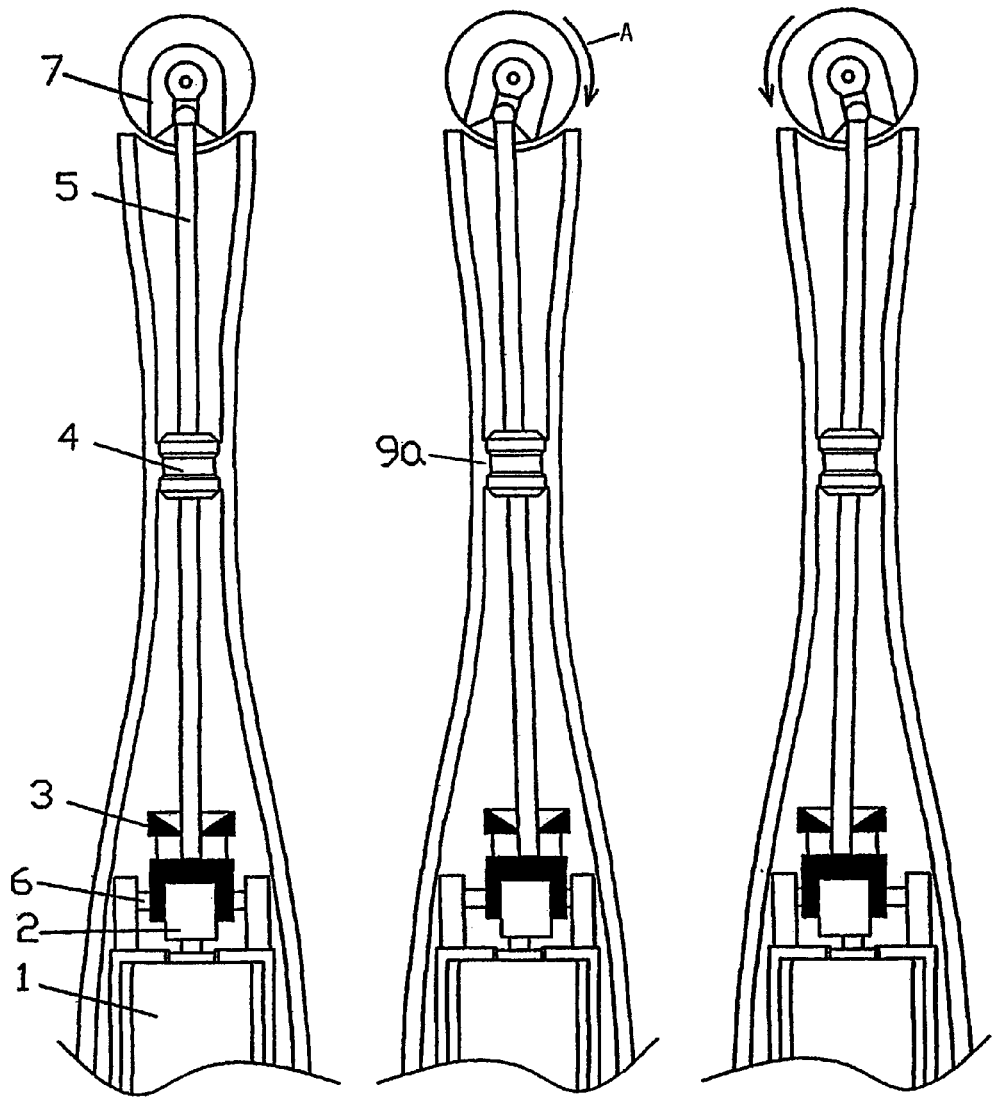
FIGS. 4a to 4c are schematic cross-sectional elevations of the neck and head portion of the toothbrush showing three different pivotal orientations of its tuft block in use.

In the accompanying drawings there is depicted schematically an electric toothbrush having a neck 9 supporting at its distal end a head 8 and extending at its proximal end from a handle 14. Within the handle 14 there is mounted an electric motor 1, batteries and a switch to activate the electric motor (batteries and switch not shown). Upon the output shaft of the electric motor 1 there is provided an eccentric cam 2 that fits within a recess 15 at the back of a cam follower 3. The cam follower 3 is mounted upon a transverse shaft 6 so as to reciprocate transversely within the handle 14 upon rotation of the cam 2. The cam 2 has a hole 2a which fits tightly upon the output shaft of the motor.

The cam follower has an aperture 3b into which the proximal end of a rocker arm 5 is received.

The rocker arm 5 extends longitudinally within the neck 9 and has a bulbous formation 5a at its distal end.

At the distal end of the neck 9, there is an attached a head 8 to which a tuft block 7 is pivotally mounted. The head 8 includes a ramped fixing tab that snap-engages within a recess inside the neck 9 upon assembly to fix the head 8 in place upon the neck 9.

The head 8 includes a number of fixed bristle tufts 8c positioned alongside those provided on the pivotal tuft block 7. There is a fixed boss 8b within the head upon which a pivot recess 7a of the tuft block 7 is mounted. About the pivot recess 7a, the tuft block includes a C-channel 7c. A retaining pin 12 extends through a side aperture 8d of the head 8 and into the C-channel to prevent the tuft block 7 from detaching from the head. A pivot pin 10 extends from the boss 8b and into the pivot recess 7a and a spring 11 surrounds the pin 10 to bias an edge of the C-channel against the retaining pin 12.

The tuft block 7 also includes a slot 7b into which the bulbous end 5a of the rocker arm is received. The slot 7b is just wide enough to receive the bulbous head 5a.

At an intermediate lengthwise location of the rocker arm 5, there is provided a resilient bushing 4 having a hole 4a through which the rocker arm 5 extends. The resilient bushing would typically be fabricated from rubber or soft plastics material. The external surface of the rocker arm is sealed against the hole 4a and once in place does not slide within the hole. The external surface of the bushing 4 is provided with an annular groove 4b that receives an internal annular ridge 9a of the neck. The bushing 4 is thereby sealed and fixed within the neck 9 and provides a pivot mounting fulcrum for the rocker arm. It to be noted that the rocker arm is not intended to rotate about its longitudinal axis and is not intended to reciprocate lengthwise. It merely rocks back and forth like a seesaw upon the resilient bushing 4. To this end, the cam follower 3 reciprocates transversely upon shaft 6 as a result of activation of motor 1 and its interaction with cam 2. As the proximal end of the rocker arm 5 is received within the aperture 3b of the cam follower, it will reciprocate transversely (sideways) whereupon the bulbous distal end 5a of the rocker arm will reciprocate transversely (sideways) in opposite phase. This transverse movement of the bulbous end 5a of the rocker arm against the sides of the slot 7b will cause pivotal oscillation of the tuft block 7 upon pin 10.

The head end of the neck and head itself are of course used in a wet environment and it is essential that liquid does not pass along the rocker arm to the electric motor 1. The resilient bushing 4 therefore provides a dual function— namely to resiliently mounted the rocker arm and provide its fulcrum and also to internally seal the distal end of the neck from the proximal end of the neck.

It should be appreciated that modifications and alterations obvious to those skilled in the art are not to be considered as beyond the scope of the present invention. For example, the specific example of a cam follower adapted to convert rotational output of the motor into sideways reciprocation of the proximal end of the rocker arm can be changed without departing from the scope of the invention.

The invention claimed is:

1. An electric toothbrush comprising:
   a casing comprising a handle and a neck extending from the handle,
   a motor situated within the handle and comprising an output shaft having an eccentric cam thereon,
   a cam follower mounted to slide upon a transverse rod, the cam follower being driven by the cam to reciprocate transversely,
   a tuft block at a remote end of the neck,
   a rocker arm extending longitudinally within the neck and having a proximal end engaging the cam follower, and a distal end driving the tuft block, and
   a resilient bushing sealed within the neck and through which an intermediate-portion of the rocker arm extends in sealed manner to allow pivoting of the rocker arm across the bushing, wherein the cam follower is reciprocated transversely by engagement with the cam, and the proximal and distal ends of the rocker arm reciprocate transversely in opposite phase about the bushing to drive the tuft block.

2. The electric toothbrush of claim 1, wherein the cam follower comprises a recess into which the cam extends.

3. The electric toothbrush of claim 1, wherein the cam follower further comprises an aperture into which the proximal end of the rocker arm is received.

4. The electric toothbrush of claim 1, further comprising a head attached to the neck, and wherein the tuft block is mounted to pivot upon the head and comprises a slot into which the distal end of the rocker arm is received.

5. The electric toothbrush of claim 4, wherein the distal end of the rocker arm is bulbous.

6. The electric toothbrush of claim 1, wherein the resilient bushing comprises an annular external groove and the neck comprises an annular internal ridge received by the groove.

7. The electric toothbrush of claim 1, further comprising a head formed integrally with the neck, and wherein the tuft block is mounted to pivot upon the head and comprises a slot into which the distal end of the rocker arm is received.

* * * * *

UNITED STATES PATENT AND TRADEMARK OFFICE
CERTIFICATE OF CORRECTION

PATENT NO. : 7,197,784 B2 Page 1 of 1
APPLICATION NO. : 10/924662
DATED : April 3, 2007
INVENTOR(S) : Wong It is certified that error appears in the above-identified patent and that said Letters Patent is hereby corrected as shown below:

On The Title Page:

In section "(30)    *Foreign Application Priority Data*"

delete "(CH)" and substitute --(CN)--.

Signed and Sealed this

Twenty-sixth Day of June, 2007

JON W. DUDAS
*Director of the United States Patent and Trademark Office*